(12) United States Patent
Anderson

(10) Patent No.: US 8,192,429 B2
(45) Date of Patent: Jun. 5, 2012

(54) ABNORMALITY ERADICATION THROUGH RESONANCE

(75) Inventor: Robert S Anderson, Livermore, CA (US)

(73) Assignee: Theravant, Inc., Livermore, CA (US)

( * ) Notice: Subject to any disclaimer, the term of this patent is extended or adjusted under 35 U.S.C. 154(b) by 66 days.

(21) Appl. No.: 12/825,394

(22) Filed: Jun. 29, 2010

(65) Prior Publication Data

US 2011/0319884 A1 Dec. 29, 2011

(51) Int. Cl.
*A61B 18/12* (2006.01)
*A61B 18/14* (2006.01)

(52) U.S. Cl. .......................................... 606/41; 606/34
(58) Field of Classification Search .............. 606/27–29, 606/32, 34, 41
See application file for complete search history.

(56) References Cited

U.S. PATENT DOCUMENTS

| | | | |
|---|---|---|---|
| 4,343,931 A | 8/1982 | Barrows |
| 5,323,778 A | 6/1994 | Kandarpa et al. |
| 6,203,537 B1 | 3/2001 | Adrian |
| 6,632,222 B1 | 10/2003 | Edwards et al. |
| 6,836,688 B2 | 12/2004 | Ingle et al. |
| 6,972,022 B1 | 12/2005 | Griffin |
| 7,229,455 B2 | 6/2007 | Sakurai et al. |
| 7,335,199 B2 | 2/2008 | Goble et al. |
| 7,483,755 B2 | 1/2009 | Ingle et al. |
| 7,498,565 B2 | 3/2009 | Silberberg et al. |
| 7,608,839 B2 | 10/2009 | Coulombe et al. |
| 2003/0050632 A1 | 3/2003 | Fjield et al. |
| 2004/0068254 A1 | 4/2004 | Hayashi et al. |
| 2006/0009750 A1 | 1/2006 | Altshuler et al. |
| 2006/0020260 A1 | 1/2006 | Dover et al. |
| 2006/0155267 A1 | 7/2006 | Berzak et al. |
| 2006/0184163 A1 | 8/2006 | Breen et al. |
| 2006/0271036 A1 | 11/2006 | Garabedian et al. |
| 2007/0027440 A1 | 2/2007 | Altshuler et al. |
| 2007/0027446 A1 | 2/2007 | Goble |
| 2007/0208363 A1 | 9/2007 | Lai |
| 2007/0264625 A1 | 11/2007 | DeBenedictis et al. |
| 2007/0264626 A1 | 11/2007 | DeBenedictis et al. |

(Continued)

FOREIGN PATENT DOCUMENTS

EP 684786 B1 10/2003

(Continued)

OTHER PUBLICATIONS

Chinnayelka S, McShane MJ., "Microcapsule biosensors using competitive binding resonance energy transfer assays based on apoenzymes", Sep. 1, 2005, pp. 1, Last Viewed Jun. 28, 2010.

(Continued)

*Primary Examiner* — Michael Peffley
*Assistant Examiner* — Samantha Good
(74) *Attorney, Agent, or Firm* — Raj Abhyanker, P.C.

(57) ABSTRACT

A medical device to eradicate abnormality is provided. In one embodiment, the medical device includes a needle and an electrode. The medical device further includes a processor to automatically determine a portion of a biological tissue is associated with an abnormality when a sample density of an immediate area surrounding the needle in the biological tissue matches a target density as determined based on one or more of a chemical composition and a pigmentation of the abnormality. The processor calculates a resonant frequency to eradicate a presence of the abnormality based on the chemical composition and/or the pigmentation of the abnormality as determined through one or more of a conductivity, a capacitance, and an inductance of the abnormality. The medical device also includes a signal source to electrically couple the needle with the electrode to form a closed circuit when the needle and electrode contact the biological tissue.

6 Claims, 14 Drawing Sheets

U.S. PATENT DOCUMENTS

| | | |
|---|---|---|
| 2008/0004621 A1 | 1/2008 | Dahla et al. |
| 2008/0058788 A1 | 3/2008 | Boyden et al. |
| 2008/0139974 A1 | 6/2008 | Da Silva |
| 2008/0167649 A1 | 7/2008 | Edwards et al. |
| 2008/0287730 A1 | 11/2008 | Spiegel |
| 2009/0137999 A1 | 5/2009 | Silberberg et al. |
| 2009/0149732 A1 | 6/2009 | Weinstock et al. |
| 2009/0163940 A1 | 6/2009 | Sliwa |
| 2009/0170105 A1 | 7/2009 | Kornman et al. |
| 2009/0175927 A1 | 7/2009 | Gammelsaeter et al. |
| 2009/0192505 A1 | 7/2009 | Askew et al. |
| 2009/0198093 A1 | 8/2009 | Meissner et al. |
| 2009/0216109 A1 | 8/2009 | Karmarkar et al. |
| 2009/0221999 A1 | 9/2009 | Shahidi |
| 2009/0253981 A1 | 10/2009 | Hamilton et al. |
| 2009/0258841 A1 | 10/2009 | Murphy et al. |
| 2009/0275899 A1 | 11/2009 | Deem et al. |
| 2009/0280153 A1 | 11/2009 | Hunter et al. |
| 2009/0281537 A1 | 11/2009 | Britva et al. |
| 2009/0318909 A1 | 12/2009 | DeBenedictis et al. |
| 2010/0016783 A1 | 1/2010 | Bourke, Jr. et al. |
| 2010/0098692 A1 | 4/2010 | Theuer et al. |
| 2010/0113423 A1 | 5/2010 | Mochly-Rosen et al. |
| 2010/0113983 A1 | 5/2010 | Heckerman et al. |

FOREIGN PATENT DOCUMENTS

| | | |
|---|---|---|
| EP | 1916013 A1 | 4/2008 |
| EP | 1848356 B1 | 11/2008 |
| EP | 1987764 A1 | 11/2008 |
| EP | 988091 B1 | 10/2009 |
| WO | 9627358 A1 | 9/1996 |
| WO | 9736619 A2 | 10/1997 |
| WO | 03096872 A2 | 11/2003 |
| WO | 2006017517 A2 | 2/2006 |
| WO | 2007041677 A2 | 4/2007 |
| WO | 2007133641 A1 | 11/2007 |
| WO | 2008002625 A2 | 1/2008 |
| WO | 2008031056 A2 | 3/2008 |
| WO | 2008065652 A2 | 6/2008 |
| WO | 2008068485 A2 | 6/2008 |
| WO | 2008070580 A2 | 6/2008 |
| WO | 2008118853 A1 | 10/2008 |
| WO | 2008124112 A1 | 10/2008 |
| WO | 2008125810 A1 | 10/2008 |
| WO | 2008131306 A1 | 10/2008 |
| WO | 2008151277 A1 | 12/2008 |
| WO | 2008154285 A1 | 12/2008 |
| WO | 2009136291 A2 | 11/2009 |
| WO | 2009139817 A2 | 11/2009 |
| WO | 2009142835 A2 | 11/2009 |
| WO | 2009145982 A1 | 12/2009 |
| WO | 2010009141 A1 | 1/2010 |
| WO | 2010009735 A2 | 1/2010 |
| WO | 2010018001 A1 | 2/2010 |
| WO | 2010039465 A2 | 4/2010 |
| WO | 2010039873 A2 | 4/2010 |
| WO | 2010054264 A1 | 5/2010 |
| WO | 2010062308 A1 | 6/2010 |
| WO | 2010063011 A2 | 6/2010 |
| WO | 2010065135 A1 | 6/2010 |

OTHER PUBLICATIONS

Van Der Velden EM, Defranq J, Baruchin AM., "Cosmetic and reconstructive medical tattooing", Curr Opin Otolaryngol Head Neck Surg. Dec. 13, 2005, (6):349-53, pp. 1, Last Viewed Jun. 28, 2010.

M Bharkatiya, RK Nema., "Skin penetration enhancement techniques", Year 2009, vol. 1, Issue : 2, p. 110-115, pp. 6, Last Viewed Jun. 28, 2010.

Whitney D. Tope, and Frank G. Shellock., "Magnetic Resonance Imaging and Permanent Cosmetics (Tattoos): Survey of Complications and Adverse Events", Journal of Magnetic Resonance Imaging 15:180-184 (2002), DOI 10.1002/jmri.10049, pp. 5, Last Viewed Jun. 28, 2010.

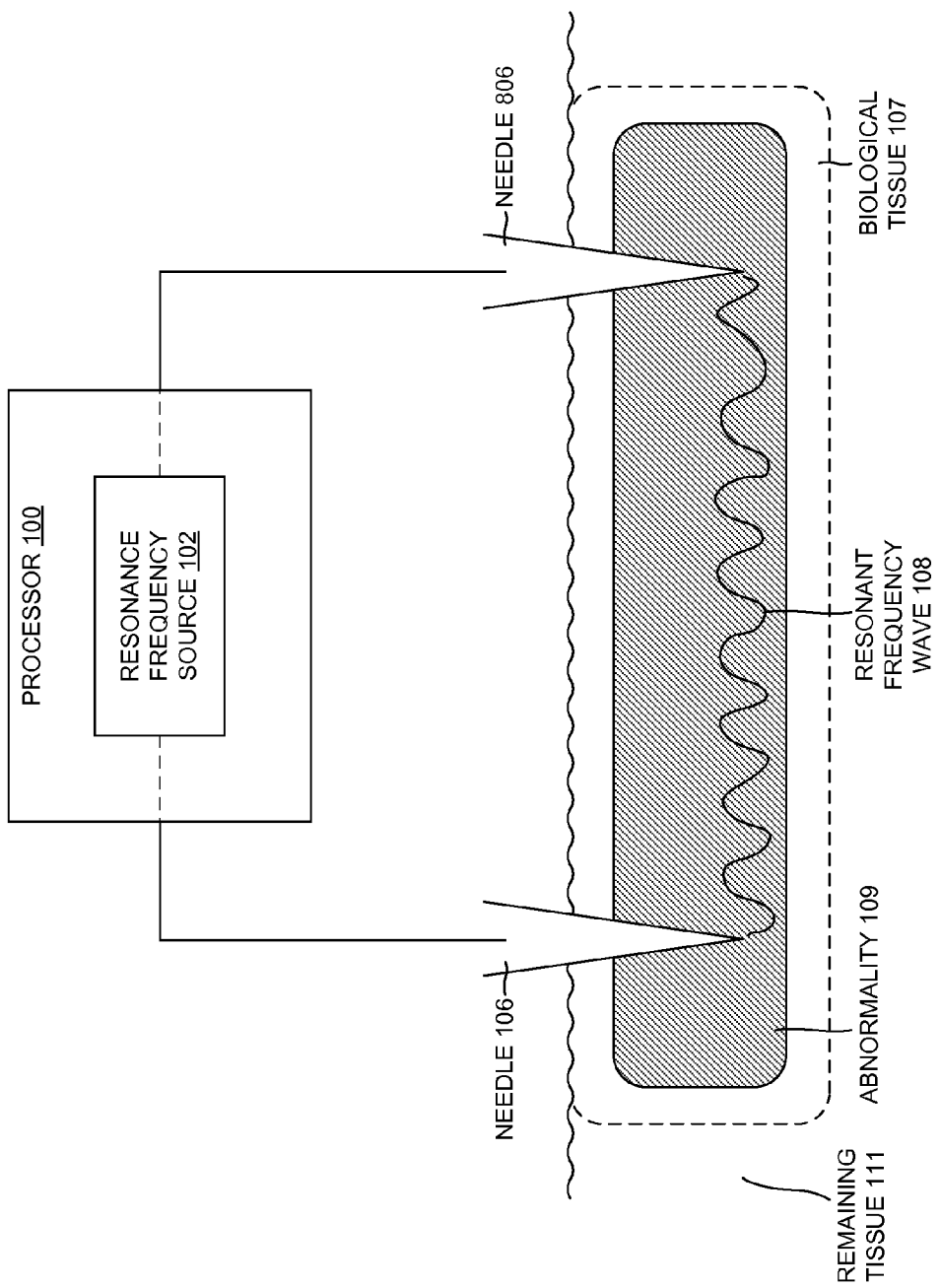

ABNORMALITY ERADICATION THROUGH RESONANCE

FIELD OF TECHNOLOGY

This disclosure relates generally to a technical field of medical treatments and, in one example embodiment, to eradication of an abnormality in a tissue through resonance.

BACKGROUND

An abnormality may appear in a biological tissue. The abnormality may appear due to cancer, exposure to sunlight, age, and/or other factors. In addition, the abnormality may appear because of submission to tattoo processes. A patient may wish to remove the abnormality from the biological tissue. Removal of the abnormality from the biological tissue may cause scarring. In some instances, removal of the abnormality may damage other biological tissue surrounding a target area.

SUMMARY

Abnormality eradication through resonance is disclosed. In one aspect, a processor of a medical device automatically determines which portion of a biological tissue is associated with an abnormality (e.g., a foreign substance, an undesired manifestation, etc.) in the biological tissue. A determination is made when a sample density of an immediate area surrounding the needle in the biological tissue matches a target density. The target density may be determined based on a chemical composition or a pigmentation of the abnormality.

The processor calculates a resonant frequency to eradicate a presence of the abnormality based on a chemical composition and a pigmentation of the abnormality as determined through an electrical property (e.g., a conductivity, a capacitance, and an inductance) of the abnormality.

The medical device includes a signal source to electrically couple the needle with the electrode such that a closed circuit is formed when the needle and electrode contact the biological tissue. The signal source of the medical device also delivers the resonant frequency targeted to the abnormality through the biological tissue in a manner such that a delivery of the resonant frequency preserves a regeneration capability of a remaining tissue surrounding the biological tissue by monitoring a vibration of the remaining tissue and/or the biological tissue when the resonant frequency is applied to the biological tissue having the abnormality.

The processor may apply an algorithm to determine a length-of-time that the resonant frequency targeted to the abnormality is delivered. The algorithm may be based on a regeneration pattern of a wound heal area encompassing the abnormality created when the abnormality was first introduced in the biological tissue. The algorithm may determine an age of when the abnormality was first introduced in the biological tissue. The algorithm may determine a depth that the needle may need to enter the biological tissue to reach the immediate area having the target density.

A waveform segmentation module of the processor may segment a resonant waveform associated with the biological tissue from another resonant waveform associated with the abnormality based on a control sample of the remaining tissue and/or the biological tissue having the abnormality. This may be performed by applying a Fourier analysis function to a combined waveform of an afflicted area targeted for eradication of the abnormality and a split function to separate the waveforms. A resonant frequency calibration module of the processor may adjust the resonance frequency targeted to the abnormality through the biological tissue in a manner such that the delivery of the resonance frequency preserves the regeneration capability of the remaining tissue surrounding the biological tissue by monitoring the vibration of the remaining tissue and/or the biological tissue when the resonance frequency is applied to the biological tissue having the abnormality.

The abnormality may be a foreign substance and/or an undesired manifestation. In one example, the abnormality may be a tattoo in a host living organism associated with the biological tissue. In alternate embodiments, the abnormality may be a cancerous tumor, acne, a lesion, a stretch mark, a skin condition, a scar, a burn, and/or an age spot.

The methods, systems, and apparatuses disclosed herein may be implemented in any means for achieving various aspects, and may be executed in a form of a machine-readable medium embodying a set of instructions that, when executed by a machine, causes the machine to perform any of the operations disclosed herein. Other features will be apparent from the accompanying drawings and from the detailed description that follows.

BRIEF DESCRIPTION OF THE VIEWS OF DRAWINGS

Example embodiments are illustrated by way of example and not limitation in the figures of accompanying drawings, in which like references indicate similar elements and in which:

FIG. 8A illustrates a medical device for eradicating an abnormality in a biological tissue, in accordance with one or more embodiments.

Other features of the present embodiments will be apparent from accompanying Drawings and from the Detailed Description that follows.

DETAILED DESCRIPTION

Disclosed are a method, system and/or a medical device to eradicate an abnormality in a tissue. Although the present embodiments have been described with reference to specific example embodiments, it will be evident that various modifications and changes may be made to these embodiments without departing from the broader spirit and scope of the various embodiments.

Figure 1:
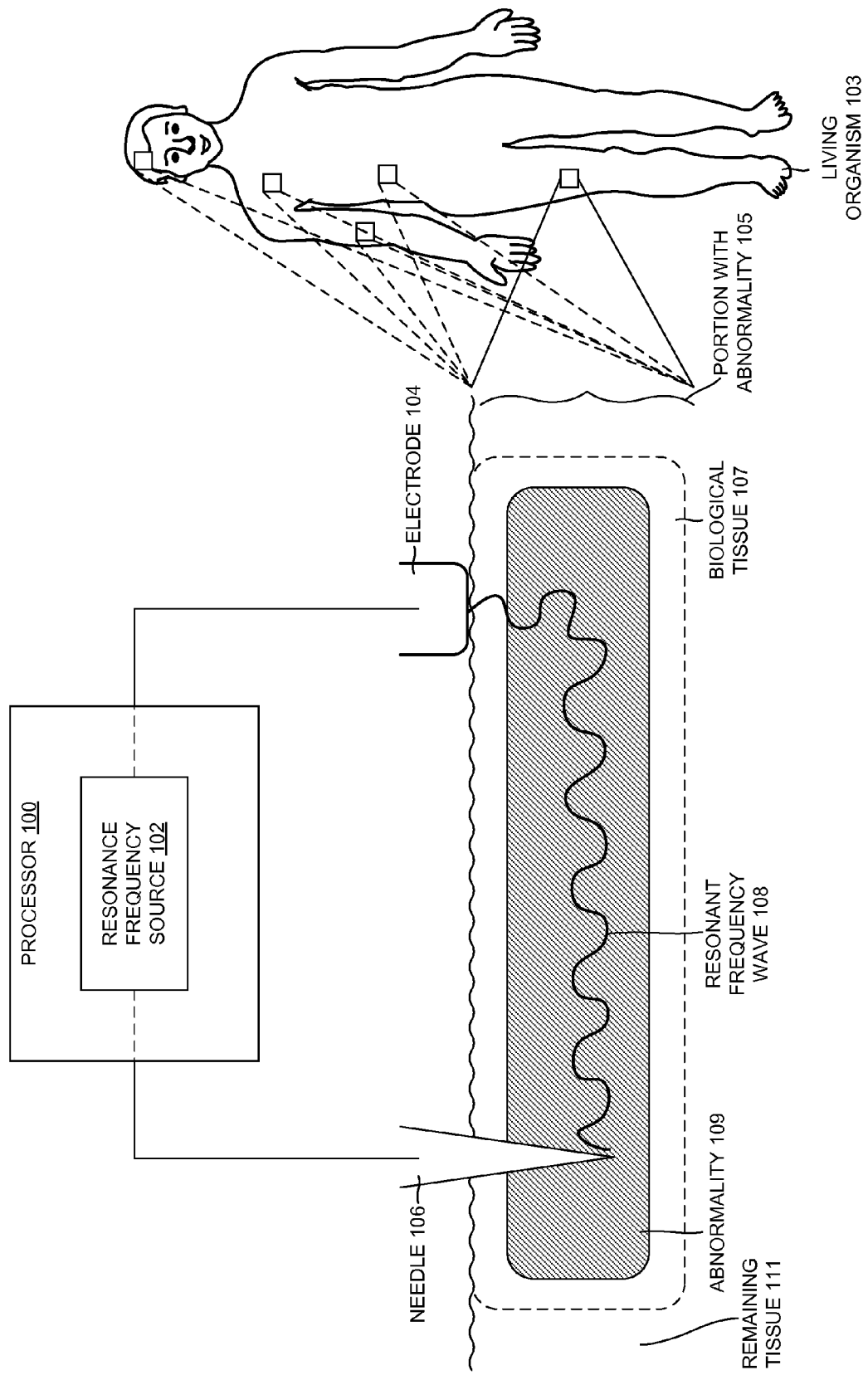
FIG. 1 illustrates a medical device to eradicate an abnormality in a tissue of a living organism in accordance with one or more embodiments.

FIG. 1 illustrates a medical device to eradicate an abnormality 109 in a tissue of a living organism 103 in accordance with one or more embodiments. Examples of the abnormality may include, but is not limited to a foreign substance (e.g. a tattoo), an undesired manifestation of the tissue, and the like. Further, examples of undesired manifestation may include, but is not limited to a cancerous tumor, acne, a lesion, a stretch mark, a skin condition, a scar, a burn, an age spot, and the like. The portion with abnormality 105 on the body of the living organism 103 may include any area on the body of the living organism 103.

In one or more embodiments, the medical device may include a processor 100 operatively coupled to a signal source (e.g., a resonance frequency source 102, a voltage source, oscillator), configured to automatically determine a portion of the tissue (e.g., biological tissue 107) associated with the abnormality 109 in the tissue and also configured to calculate a resonance frequency to eradicate a presence of the abnormality 109 based on chemical composition and/or pigmentation of the abnormality 109. As used herein the term "biological tissue" refers to the tissue with the abnormality 109.

Further, the signal source and/or the resonance frequency source 102 may be configured to deliver a resonance frequency targeted to the abnormality 109 in a manner such that a delivery of the resonance frequency preserves a regeneration capability of a remaining tissue 111 surrounding the biological tissue 107 by monitoring a vibration of the remaining tissue 111 and/or the biological tissue 107 when the resonance frequency is applied to the biological tissue 107 having the abnormality, while eradicating the abnormality 109. As used herein the term "remaining tissue" refers to a region on the tissue of the living organism 103 devoid of any abnormality. The processor 100 may be configured to determine the portion of the biological tissue 107 associated with the abnormality 109 when a sample density of an area on the tissue matches a target density. In one or more embodiments, the target density may be determined based on a chemical composition and/or pigmentation of the abnormality. In one or more embodiments, the resonance frequency source 102 may be coupled to an electrode 104 and/or a needle 106 such that a closed circuit is formed when the needle 106 and the electrode 104 contact the tissue (e.g. the biological tissue 107 of the living organism 103). The needle 106 and the electrode 104 may be positioned on a portion with abnormality 105 and the needle 106 may puncture through a portion of the biological tissue 107 with the abnormality.

A resonance frequency waveform 108 generated from the resonance frequency source 102 flowing between the needle 106 and the electrode 104 forms the closed path. The resonance frequency flowing through the abnormality 109 may eradicate the abnormality 109, while the remaining tissue 111 may remain unaffected. The chemical composition and/or pigmentation may be determined based on conductivity, capacitance, and/or inductance of the abnormality 109.

Figure 2:
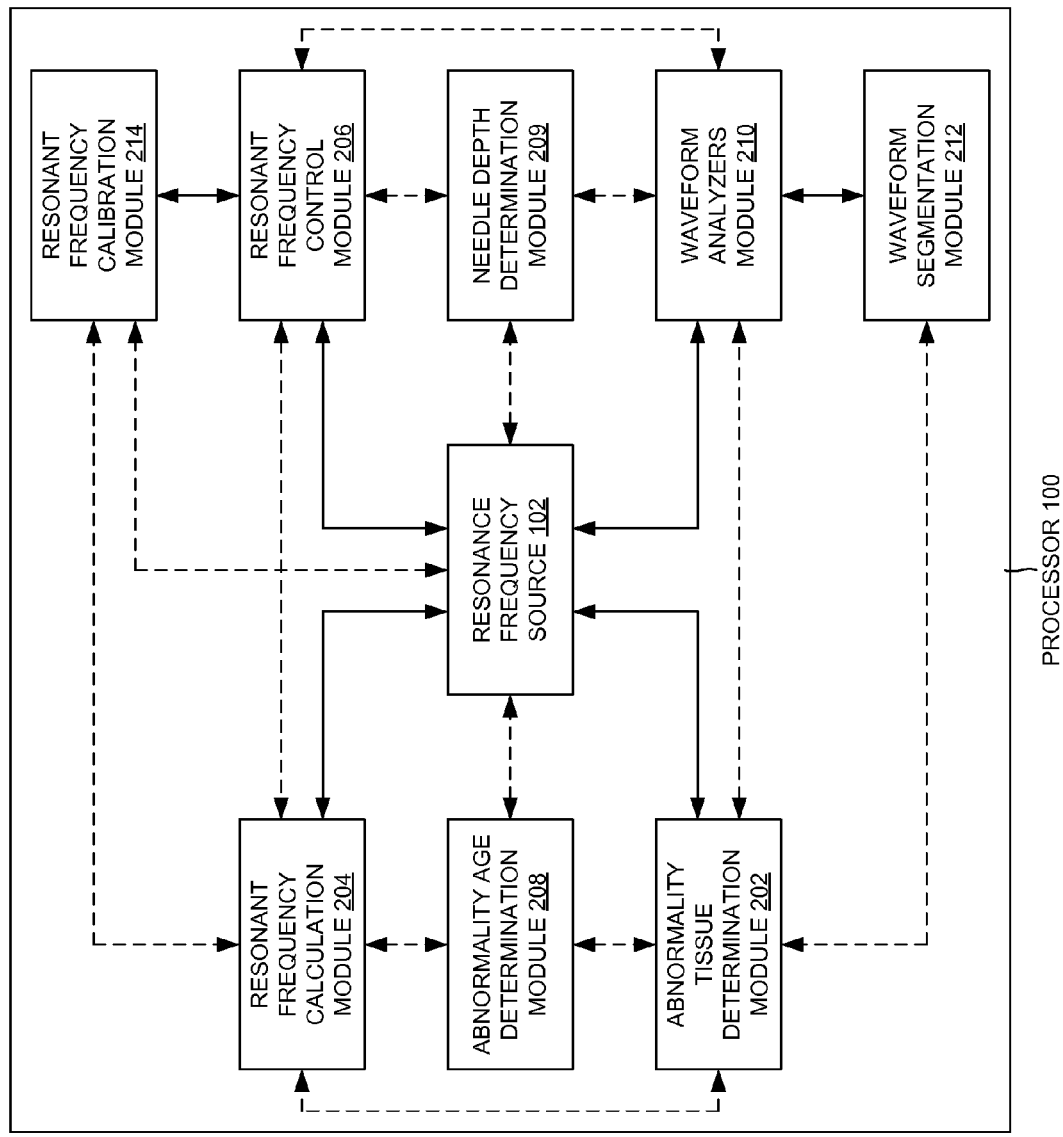
FIG. 2 illustrates a block diagram of the processor of the medical device of FIG. 1, in accordance with one or more embodiments.

FIG. 2 is a block diagram of the processor 100 of the medical device of FIG. 1, in accordance with one or more embodiments. In one or more embodiments, the processor 100 may be operatively coupled to the resonance frequency source 102. The resonance frequency source 102 may be within or may be external to the processor 100. The resonance frequency source 102 may be configured to generate a resonant waveform to be applied to the abnormality 109 in the biological tissue 107 to eradicate the abnormality 109. In one or more embodiments, the processor 100 may be configured to control and/or coordinate with the resonance frequency source 102. The processor 100 may be configured to determine a portion of the biological tissue 107 associated with the abnormality 109. In one or more embodiments, the processor 100 may include an abnormality tissue determination module 202 configured to automatically determine the portion of the biological tissue 107 associated with the abnormality 109 in the biological tissue 107. The abnormality tissue determination module 202 may determine the abnormality 109 by matching a sample density of an immediate area surrounding the needle 106 in the biological tissue 107 with a target density.

The sample density and/or the target density may be determined based on a chemical composition and/or a pigmentation of the abnormality 109. In one or more embodiments, the processor 100 may also include a resonance frequency calculation module 204 to calculate a resonance frequency based on the chemical composition and/or the pigmentation of the abnormality 109 to eradicate a presence of the abnormality. The pigmentation and/or the chemical composition may be determined through a conductivity, a capacitance, and/or an inductance of the abnormality. The processor 100 may further include a resonance frequency control module 206 configured through one or more algorithms to determine a length of time for which the resonance frequency targeted to the abnormality 109 is delivered, in other words, to determine the length of time of exposing the biological tissue 107 to the resonant waveform generated by the resonance frequency source 102. The algorithm may be based on a regeneration pattern of a wound heal area encompassing the abnormality 109, created when the abnormality 109 was first introduced in the biological tissue 107.

In one or more embodiments, the processor 100 may further include an abnormality age determination module 209 configured through an algorithm/multiple algorithms to determine age of the abnormality 109. The age of the abnormality 109 may be determine based on one or more factors, including but not limited to, thickness of the abnormality, elasticity of the abnormality, pigmentation of the abnormality, and the like. The abnormality age determination module 209 may use one or more techniques include, for example, dermal echogenicity to determine the age of the abnormality 109. In one or more embodiments, the process of determining the age of the abnormality 109 may involve using needle in contact with the abnormality to determine depth of the abnormality 109. Based on the determined age of the abnormality 109, the resonance frequency source 102 may coordinate with the abnormality age determination module 208 to determine a suitable resonance frequency required to eradicate the abnormality 109. Also, depending on the type and/or age of the abnormality, the amount of exposure to the resonance frequency signal required by the abnormality 109 in order to eradicate the abnormality 109 may vary. The amount of exposure required may also depend on depth at which the needle 106 is inserted into the abnormality. For example, the needle 106 inserted 20 micro meters deep into the biological tissue may allow passage of the resonance frequency through more number of skin cells than the needle 106 inserted 10 micro meters deep, and thereby destroying more number of skin cells.

In one or more embodiments, the processor 100 may also include a needle depth determination module 209 configured to determine a depth at which the needle 106 must be inserted into the abnormality 109 in the biological tissue 107. The depth may depend on depth of the abnormality 109 in the biological tissue 107 and/or the location where the resonance frequency needs to be applied so that the regeneration capacity of the remaining tissue 111 is intact. In one or more embodiments, each material may have a resonance frequency waveform specific to the characteristics of the material. For example, a red tattoo pigment may have a specific resonance frequency waveform which may be different from the resonant frequency waveform of a blue tattoo pigment. The resonant frequency of a specific material may not destroy any material other than the specific material to which the resonant frequency is specific. As a result, in one or more embodiments, to eradicate the abnormality 109 while preserving the regeneration capacity of the remaining tissue 111, determining an exact resonance frequency waveform 108 of the abnormality 109 may be required. The exact resonance frequency waveform 108 may be communicated to the resonance frequency source 102 after the exact resonance frequency of the abnormality 109 may be determined. In one or more embodiments, the resonance frequency source 102 may generate a resonance frequency waveform 108 and transmit it through the needle 106 to form a closed circuit. In one or more embodiments, the exact resonance frequency waveform 108 may be determined by the resonant frequency calculation module 204, resonant frequency calibration module 214 and/or resonant frequency control module 206 operating in concert.

In one or more embodiments, the processor 100 may include a waveform analyzer module 210 configured to analyze the resonant waveform of the biological tissue 107 and/or the remaining tissue 111 in order to determine the resonant waveform of the abnormality 109. The resonance frequency of the abnormality 109 may be determined by segmenting the resonant waveform associated with the biological tissue 107 from the resonant waveform associated with the abnormality 109. In one or more embodiments, the processor 100 may include a waveform segmentation module 212 configured to segment the resonant waveform associated with the biological tissue 107 from the resonant waveform associated with the abnormality 109. The waveform segmentation module 212 may apply a Fourier analysis function (e.g. a discrete Fourier transform) to a combined waveform of the biological tissue 107 targeted for eradication of the abnormality 109. Further, the waveform segmentation module 207 may apply a split function to the combined waveform of the biological tissue 107 after applying the Fourier analysis function. The split function may separate the resonant frequency waveform 108 of the abnormality 109 from the combined waveform 1100. Further, the waveform analyzer module 210 may coordinate with the waveform segmentation module 212 to gather information regarding the characteristics of the combined waveform 1100. If the resonance waveform of the biological tissue 1100 is a combined waveform of the resonance frequency waveform 108 of the abnormality 109 and the resonance frequency waveform 1102 of the remaining tissue 111, then the waveform segmentation module may be used to segment the combined waveform 1100.

In addition, during exposing the abnormality 109 to the resonance frequency, the processor 100 may be configured to preserve a regeneration capability of the remaining tissue 111 devoid of abnormality 109, in the vicinity of the biological tissue 107. In one or more embodiments, the processor 100 may include a resonance frequency calibration module 214 configured to adjust the resonance frequency targeted to the abnormality 109 in a manner such that the delivery of the resonance frequency preserves the regeneration capability of the remaining tissue 111 surrounding the biological tissue 107. In one or more embodiments, the resonance frequency calibration module 214 may monitor vibration of the remaining tissue 111 and/or the biological tissue 107 when the resonance frequency is applied to the biological tissue 107 having the abnormality 109, to adjust the resonance frequency targeted to the abnormality 109. For example, if the monitored vibration of the remaining tissue 111 exceeds a threshold indicating that the applied resonance frequency is capable of causing destruction to the remaining tissue, the resonance frequency calibration module 214 may automatically signal the resonance frequency source 102 to reduce the resonance frequency. The resonance frequency calibration module 214 may coordinate with the resonance frequency source 102 to control the resonance frequency generated by the resonance frequency source. Alternately, in one or more embodiments, the resonance frequency calibration module 214 may coordinate with the resonance frequency calculation module 204 to control the resonance frequency generated by the resonance frequency source 102.

The resonance frequency source 102 generates the resonance frequency and delivers through the closed circuit as illustrated in FIG. 1. In one or more embodiments, the abnormality tissue determination module 202 may also be operatively coupled to the resonance frequency source 102 to indicate the location and type of the abnormality to aid the resonance frequency source 102 to determine the resonance frequency to be generated based on the abnormality. In one or more embodiments, the abnormality tissue determination module 202 may be directly coupled to the resonance frequency calculation module 204 and or the resonance frequency control module 206. In one or more embodiments, the waveform analyzer module 210 may also be coupled to the abnormality tissue determination module 202. In one or more embodiments, the waveform analyzer module 210 may analyze all waveforms generated from the resonance frequency source 102 and the analysis may be used to determine an appropriate waveform for a given abnormality 109 in the biological tissue 107.

Figure 3:
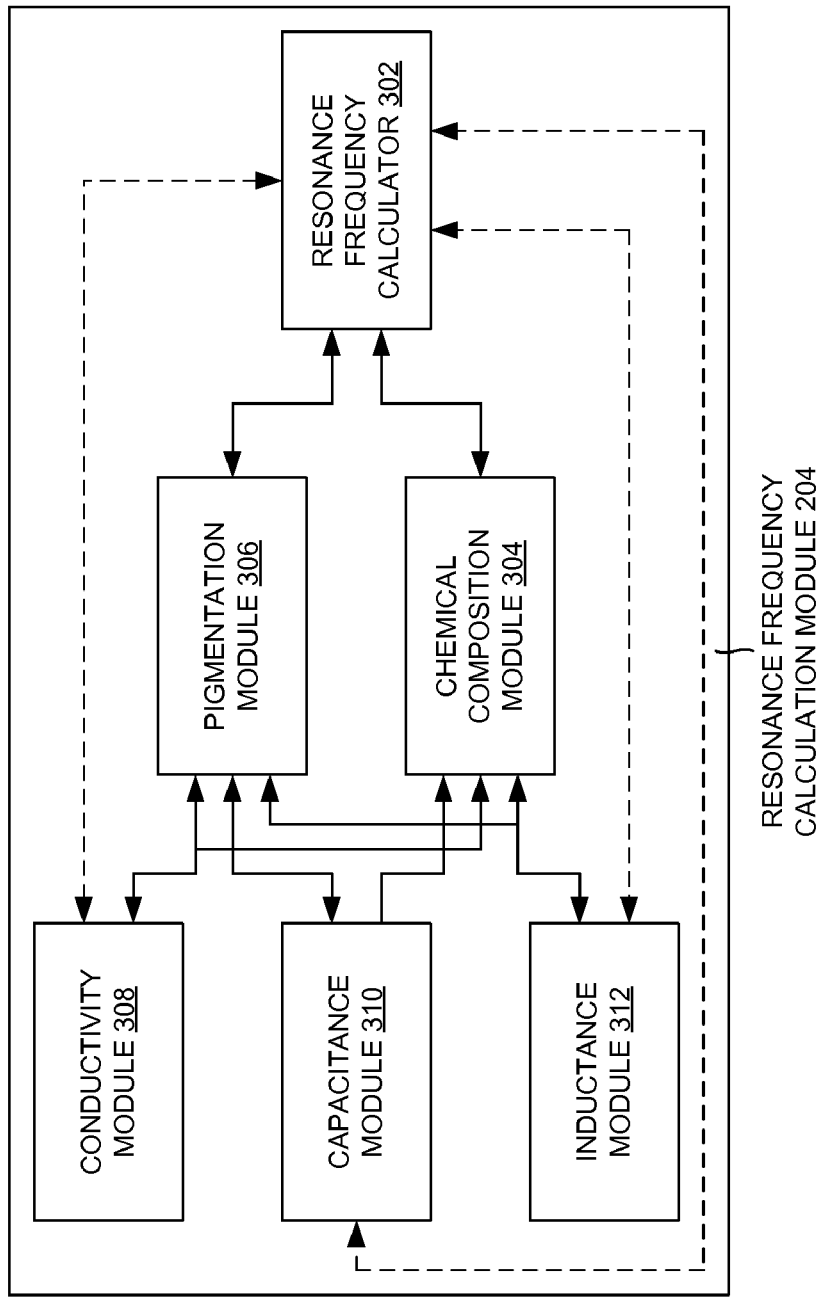
FIG. 3 illustrates a block diagram of a resonance frequency calculation module, of FIG. 2, in accordance with one or more embodiments.

FIG. 3 illustrates a block diagram of a resonance frequency calculation module 202, of FIG. 2, in accordance with one or more embodiments. In one or more embodiments, the resonance frequency calculation module 202 may include a resonance frequency calculator 302. The resonance frequency calculator 302 may be configured to calculate a resonance frequency based on the chemical composition and/or the pigmentation of the abnormality 109 in the biological tissue 107. In one or more embodiments, the resonance frequency calculation module 204 may also include a pigmentation module 306 configured to determine pigmentation of the biological tissue 107. The resonance frequency calculator 302 may be operatively coupled with the pigmentation module 306. In one or more embodiments, the resonance frequency calculation module 204 may also include a chemical composition module 304 configured to determine chemical composition of the tissue including, but not limited to the abnormality 109 and/or the biological tissue 107. The resonance frequency calculator 302 may be coupled to a chemical composition module 304. In one or more embodiments, the chemical composition and/or the pigmentation of the biological tissue 107 may be determined by the chemical composition module 304 and the pigmentation module 306 respectively based on the conductivity, capacitance, and/or inductance of the biological tissue 107. In one or more embodiments, the pigmentation module 306 and/or the chemical composition module 304 may be operatively coupled to a conductivity module 308 configured to determine the conductivity of the biological tissue 107. Also, in one or more embodiments the pigmentation module 306 and/or the chemical composition module 304 may be operatively coupled to a capacitance module 310 configured to determine capacitance of the biological tissue 107. Further, in one or more embodiments, the pigmentation module 306 and/or the chemical composition module 304 may be operatively coupled to an inductance module 312 configured to determine inductance of the biological tissue 107.

Figure 4:
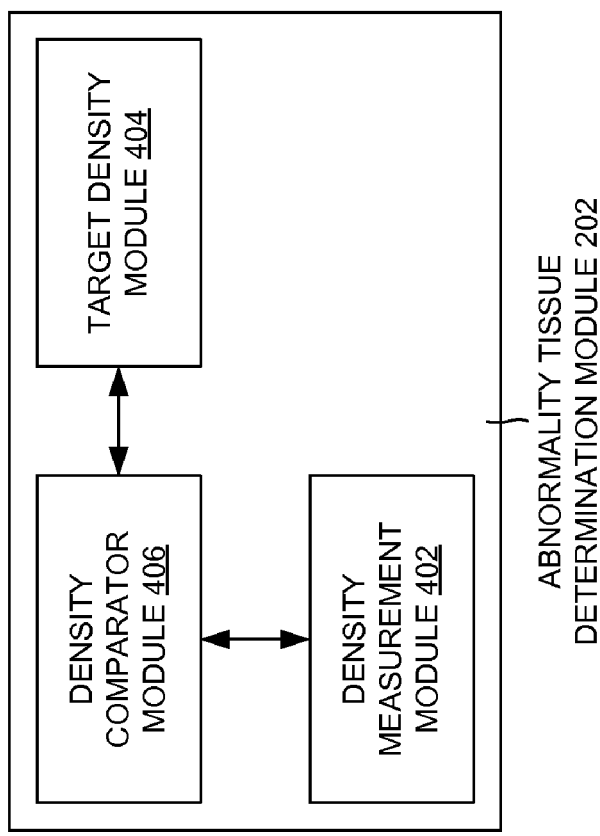
FIG. 4 illustrates a block diagram of an abnormality tissue determination module, in accordance with one or more embodiments.

FIG. 4 is a block diagram of an abnormality tissue determination module 202, in accordance with one or more embodiments. In one or more embodiments, the abnormality tissue determination module 202 may include a density measurement module 402 to determine density of various sections of a biological tissue 107. The determined density may be utilized by the abnormality tissue determination module 202 to determine an exact location and/or boundary of abnormality 109 in the biological tissue 107. Further, the abnormality tissue determination module 202 may also include a target density module 404 configured with a predetermined target density of the abnormality 109 in the biological tissue 107. In one or more embodiments the target density may be manually set. In one or more other embodiments, the target density module 404 may be preconfigured with a set of target densities for a set of abnormalities. The abnormality tissue determination module 208 may also include a density comparator module 406 configured to compare the density measured through the density measurement module 402 with the target density in the target density module 404. The abnormal tissue determination module 208 may determine location and/or boundary of the abnormality 109 in the biological tissue 107 based on the comparison. For example, the abnormality 109 may have a high density when compared to the remaining tissue 111 in the vicinity of the abnormality 109. If the threshold density of the density of the remaining tissue 111, then if the measured density exceeds the threshold density in a region within the biological tissue 107, then the abnormal tissue determination module 208 may identify the region as the abnormality 109.

Figure 5:
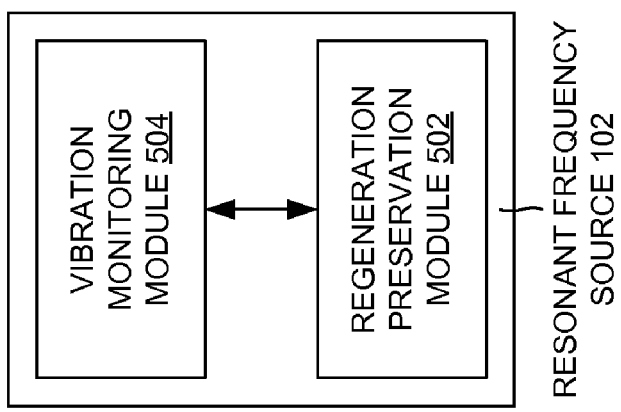
FIG. 5 illustrates a block diagram of a resonance frequency source, in accordance with one or more embodiments.

FIG. 5 is a block diagram of a resonance frequency source 102, in accordance with one or more embodiments. In one or more embodiments, the resonance frequency source 102 may include a vibration monitoring module 504 and/or a regeneration preservation module 502. The vibration monitoring module 504 may be configured to monitor vibration the remaining tissue 111 and/or the biological tissue 107 when the resonance frequency is applied to the abnormality 109 in the biological tissue 107. In one or more embodiments, the resonance frequency calibration module 214 may be operatively coupled to the vibration monitoring module 504 to control the resonance frequency based on the vibration of the remaining cells 111 monitored by the vibration monitoring module 504. The regeneration preservation module 502 may be configured to monitor any change in the regeneration capability of the remaining tissue 111 upon exposure to the resonance frequency 108 of the biological tissue 107. If the regeneration preservation module 502 determines a change in the regeneration capability, the regeneration preservation module may communicate the change to the resonance frequency calibration module 214 to control the resonance frequency generated by the resonance frequency source. In one or more embodiments, the resonance frequency calibration module 214 may be internally coupled to the resonance frequency source 102.

Figure 6:
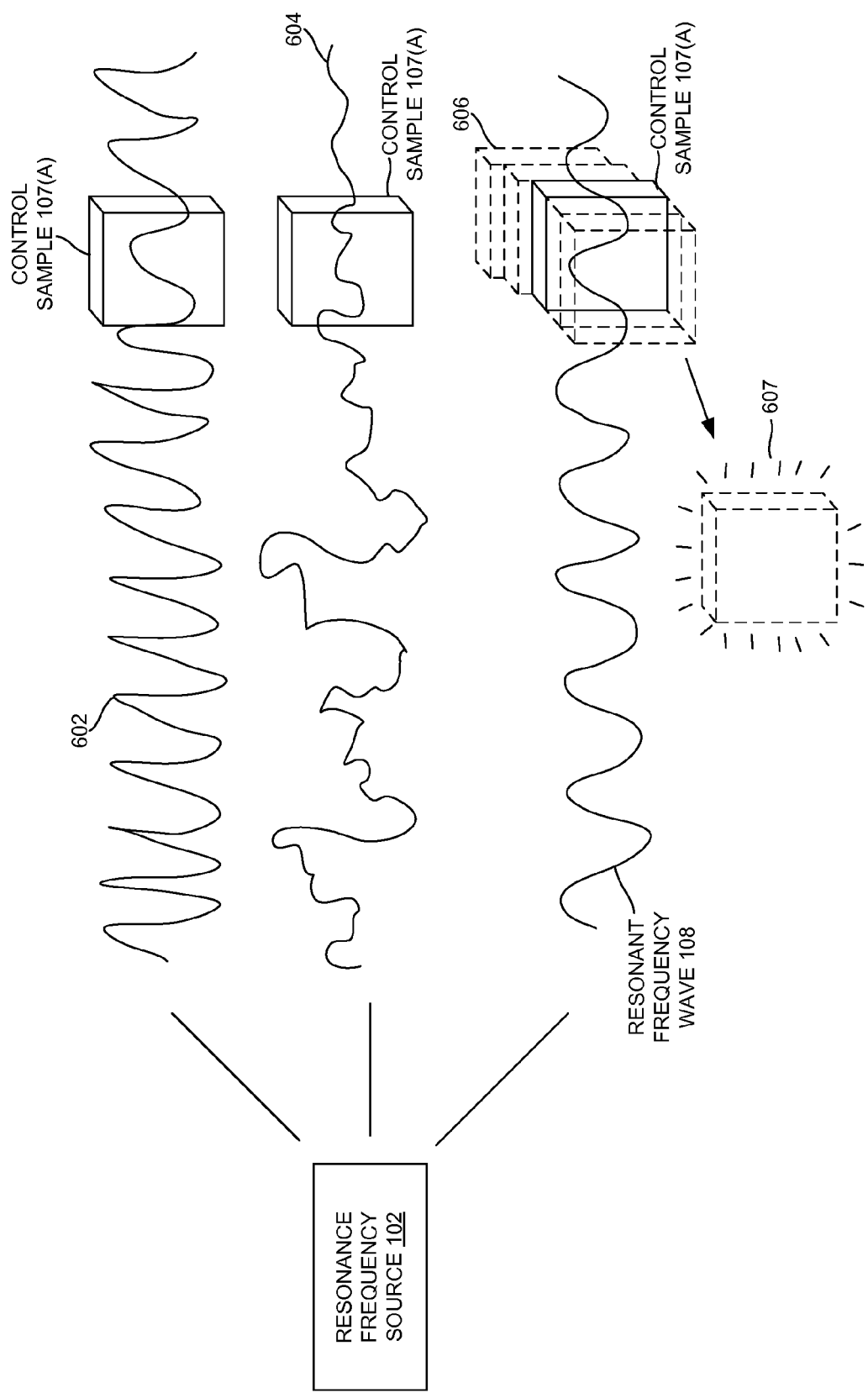
FIG. 6 illustrates an example scenario of determining a characteristic resonance frequency of a control sample, in accordance with one or more embodiments.

FIG. 6 illustrates an example scenario of determining a characteristic resonance frequency of a control sample 107 (A), in accordance with one or more embodiments. The control sample 107(A), may be a sample of a tissue, including but not limited to biological tissue 107 and/or remaining tissue 111. In the example scenario, the control sample 107 (A) may be exposed to multiple resonance frequencies generated by the resonance frequency source 102. When the control sample 107 (A) is exposed to a frequency waveform 602, the control sample may remain unaffected as the frequency waveform 602 may be greater than the characteristic resonance frequency of the control sample 107 (A). The control sample may then be exposed to a second frequency waveform 604 lower than the characteristic resonance frequency of the control sample 107 (A) and the control sample 107 (A) may continue to remain unaffected. When the control sample 107 (A) is exposed to a frequency waveform 108 which may be the resonance frequency of the control sample 107 (A), the control sample 107 (A) may vibrate. The vibration is indicated by 606 in FIG. 6. The vibration 606 may cause the control sample 107 (A) to get eradicated. An eradication of the tissue may be illustrated by 607 in FIG. 6.

Figure 7:
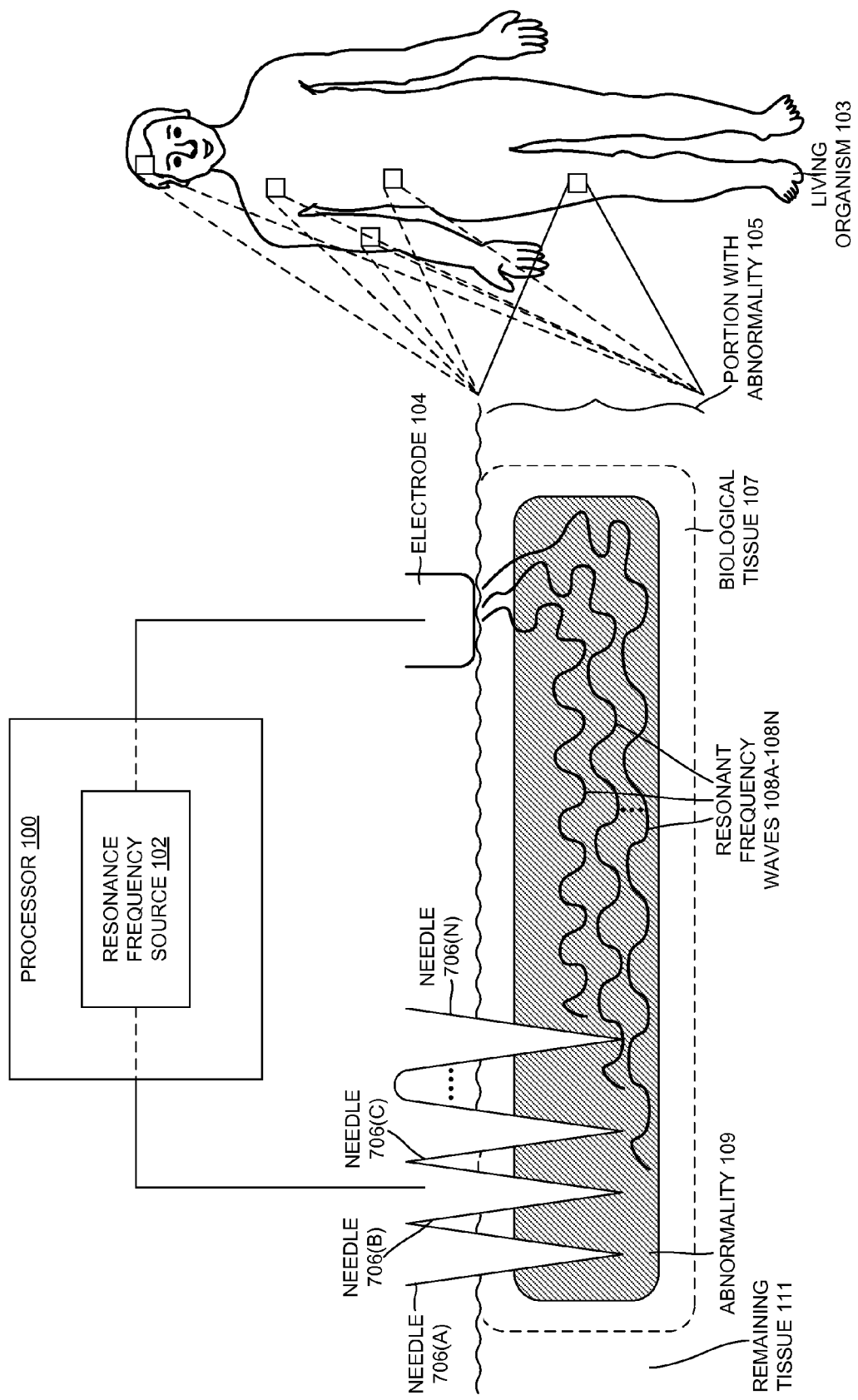
FIG. 7 illustrates medical device of FIG. 1 with multiple needle, in accordance with one or more embodiments.

FIG. 7 illustrates medical device of FIG. 1 with multiple needles (e.g., needle 706 A, needle 706 B, needle 706 C and needle 706 N), in accordance with one or more embodiments. Herein, multiple instances of like objects are denoted with reference numbers, identifying the object and parenthetical numbers and/or subscripts identifying the instance where needed. In one or more embodiments, each of the needles (706 A-706 N) may be inserted into the abnormality 109 in the biological tissue 107 of the living organism 103 at different depths. In one or more embodiments, the needles (706 A-706 N) may be inserted at a common depth. Each of the needles (706 A-706 N) may form a closed circuit with the resonance frequency source 102, the electrode 104, and the abnormality 109. Each of the closed circuits may transmit same or different resonance frequency waves (108A-108N) through the abnormality 109. In one or more embodiments, different resonant frequencies may be propagated from one needle and electrode pair from among a plurality of needles coupled to the electrode. In one or more embodiments, different resonant frequencies may be propagated between different needle and electrode pairs. In one more embodiments, the resonant frequency propagated between the needle and the electrode may be based on the characteristic of the abnormality 109.

FIG. 8A illustrates a medical device for eradicating an abnormality 109 in a biological tissue 107, in accordance with one or more embodiments. Examples of the abnormality 109 may include, but is not limited to a foreign substance (e.g. a tattoo), an undesired manifestation of the tissue, and the like. Further, examples of undesired manifestation may include, but is not limited to a cancerous tumor, acne, a lesion, a stretch mark, a skin condition, a scar, a burn, an age spot, and the like. In one or more embodiments, the medical device may include a resonance frequency source 102 with a pair of leads coupled to a pair of needles (e.g. needle 106 and needle 806). The needles may be inserted into the abnormality 109 in the biological tissue 107. The processor 100, and the needles 106 and 806 form a closed circuit through the abnormality 109 when a resonance frequency 108 is propagated between the needle pair 106 and 806, by the resonance frequency source 102.

In one or more embodiments, if the generated resonance frequency matched a characteristic resonance frequency of the abnormality 109, the abnormality may be eradicated. In one or more embodiments, the medical device may also include a processor 100 configured to control the generation of the resonance frequency waveform 108 from the resonance frequency source 102. The processor 100 may be configured through one or more algorithms. In one or more embodiments, the processor 100 may be configured to determine the portion of the biological tissue 107 associated with the abnormality 109 when a sample density of an area on the tissue matches a target density. In one or more embodiments, the target density may be determined based on a chemical composition and/or pigmentation of the abnormality.

Figure 8B:
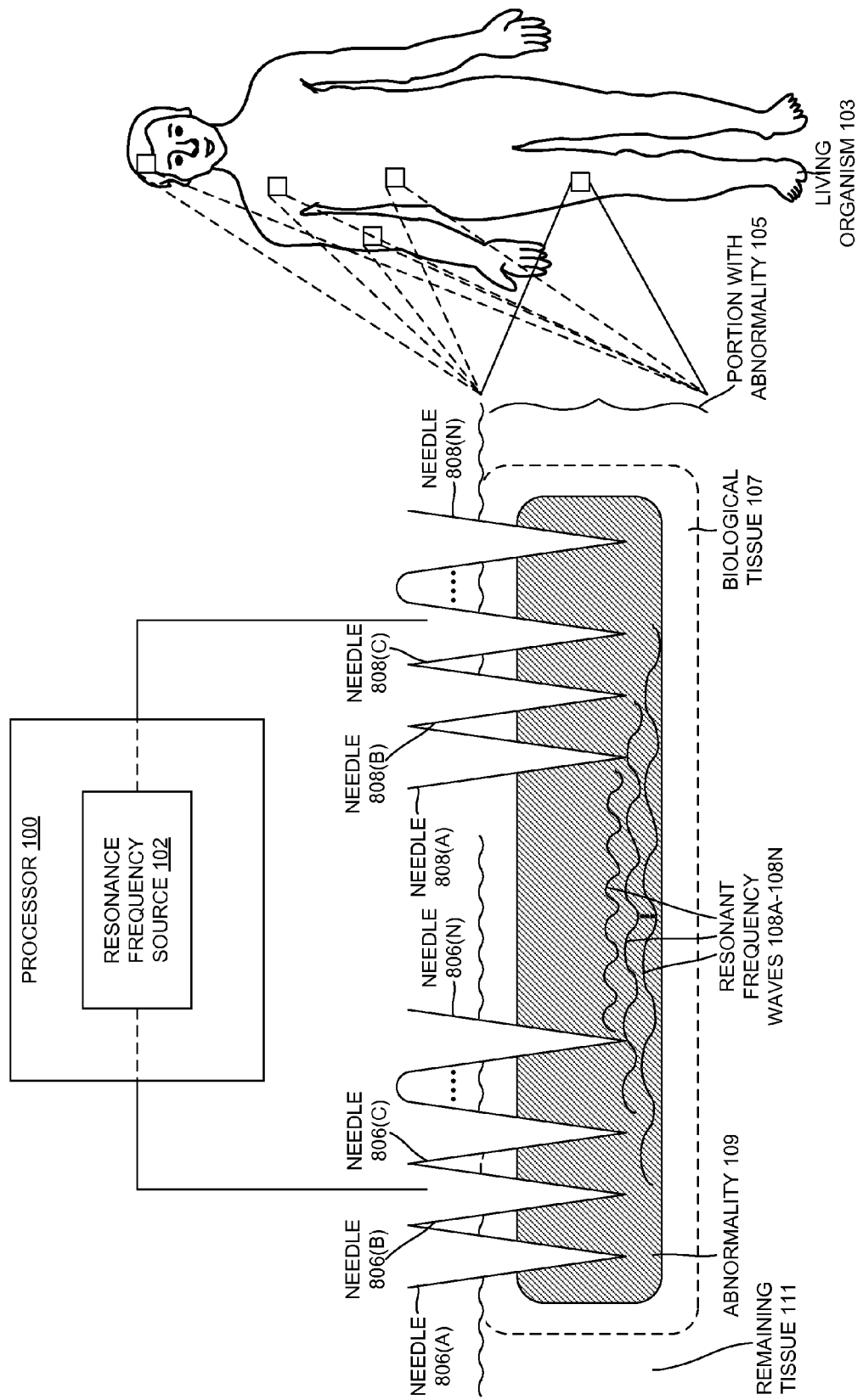
FIG. 8B illustrates a medical device for eradicating an abnormality in a biological tissue, including multiple set of needles, in accordance with one or more embodiments.

FIG. 8B illustrates a medical device for eradicating an abnormality 109 in a biological tissue 107, including multiple set of needles (806 A-806 N and 808 A-808 N) in accordance with one or more embodiments. In one or more embodiments, the medical device may include a resonance frequency source 102 with a first lead coupled to a first set of multiple needles (806 A-806 N) and a second lead coupled to a second set of needles (808 A-808 N) as illustrated in FIG. 8B. In one or more embodiments, the multiple set of needles may be inserted into the abnormality 109 of the biological tissue 107 to form multiple closed circuits through the abnormality 109 as illustrated in FIG. 8B. The resonance frequency source 102 and each needle from the first set of needles (806 A-806 N) may form a closed circuit with one of the needles from the second set of needles (808 A-808 N) through the abnormality 109, when a resonance frequency waveform 108 is propagated through the abnormality 109 in the biological tissue 107. The resonance frequency waveform is generated and propagated by the resonance frequency source 102. In one or more embodiments, one or more resonance frequency waves (e.g., 108A-108 N) may be applied to the abnormality 109.

Figure 9:
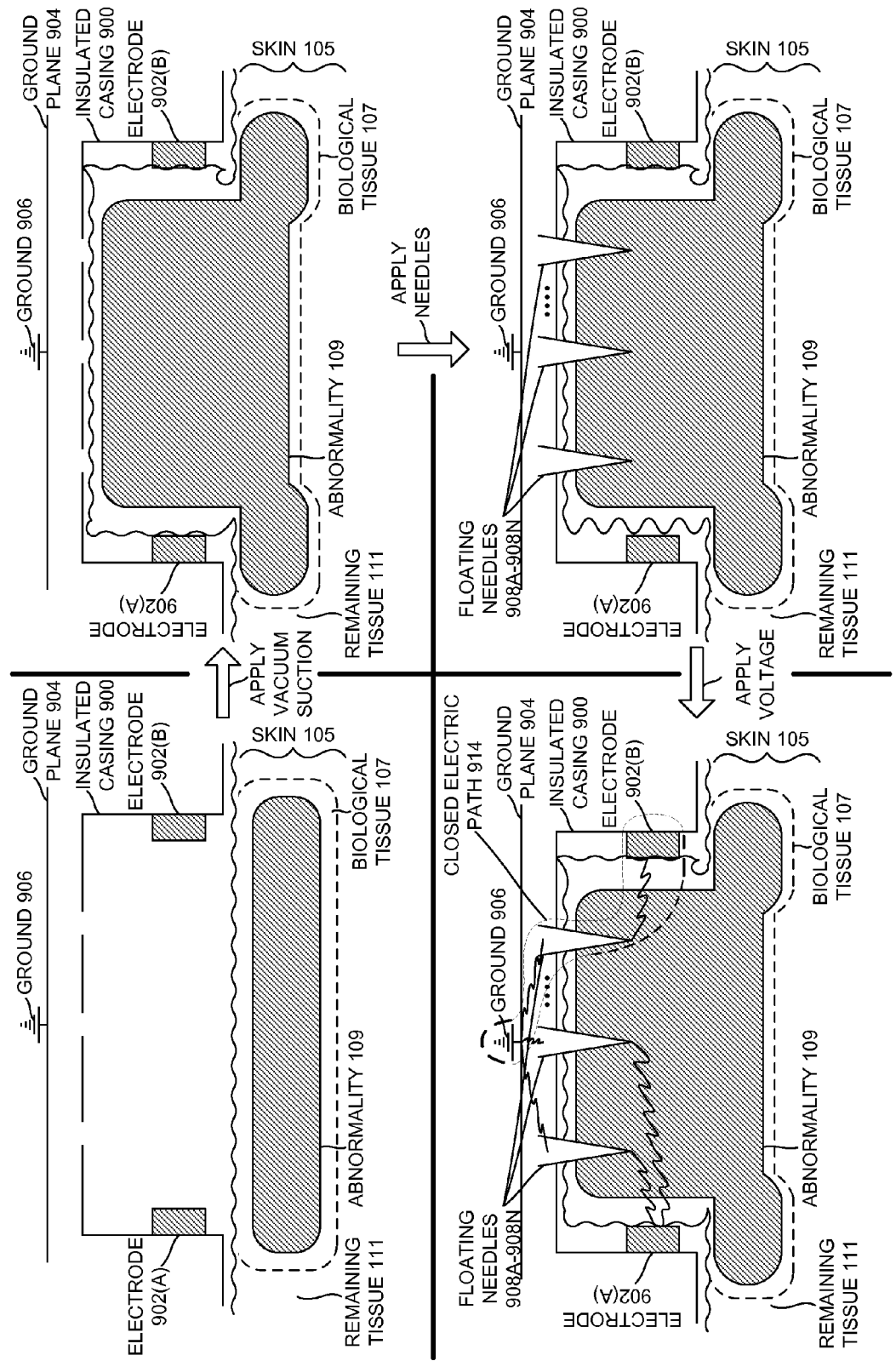
FIG. 9 illustrates an example scenario of eradication of an abnormality in a biological tissue by applying resonance frequency through a signal source, in accordance with one or more embodiments.

FIG. 9 illustrates an example scenario of eradication of an abnormality 109 in a biological tissue 107 by applying resonance frequency through a signal source, in accordance with one or more embodiments. In one or more embodiments, a medical device illustrated in FIG. 9 may be used to eradicate the abnormality 109. In one or more embodiments, the medical device may include an insulated casing 900. The insulated casing may be coupled to a pair of electrodes 902 (A) and 902 (B) maintained at a same potential which is different from the potential of a ground 906. The ground plane 904 is maintained at the potential of the ground 904 to which it is coupled. In one or more embodiments, the abnormality 109 and/or biological tissue 107 may be sucked into the insulated casing 900 through applying a vacuum suction. In one or more embodiments, the insulated casing 900 may include one or more opening for inserting one or more floating needles 908A-908N into the openings. The needles are termed floating needles because they may not be physically coupled to any hardware to deliver a flow of energy. The flow of energy may be an electric energy and/or signal energy. In one or more embodiments, when the biological tissue 107 and/or the abnormality 109 is sucked into the insulated casing 900, the abnormality 109 and/or the biological tissue 107 may come in contact with the electrodes 902(A) and 902(B). In one or more embodiments, once the abnormality 109 is sucked into the insulated casing 900, the floating needles (908A-908N) may be inserted into the abnormality though the openings in the insulated casing 900. After inserting the floating needles (908A-908N), a potential difference may be applied between the electrodes 902 (A) and 902 (B) and ground plane 906. On applying the potential difference, an electric energy flow may be produced between a first pair of electrode 902(A) and ground plane 906 and a second pair of electrode 902(B) and ground plane 906. The electric energy may not flow between the electrodes 902(A) and 902(B) as they both are maintained at the same potential. For example, 902(A) and 902(B) are both maintained at a positive potential and the ground is at a negative potential. The potential difference may be set so as to match a characteristic resonance frequency of the abnormality 109. The electric energy forms a closed electric path 914 between the electrode 902(A) and the ground plane 906 through the abnormality 109 and/or one among a plurality of floating needles. The closed electric path is illustrated by 914 in FIG. 9. A second closed electric path may be formed between the electrode 902(B) and the ground plane 906 through the abnormality 109 and/or one among a plurality of floating needles. As electric energy flows from a higher potential to a lower potential, a closed electric path 914 may be formed though the floating needles even though they are not physically coupled to any hardware. The electric energy may involuntarily form a path from the floating needles to the ground plane as the ground plane 906 is maintained at a potential opposite to that of the electrodes 902(A) and 902 (B). The electric energy may choose a path of least resistance. If the abnormality 109 is of lesser resistance then the electric energy may form a closed path through the abnormality 109. As the electrical energy passes through the abnormality 109, the electric energy may be dissipated as heat and they heat may enable the eradication of the abnormality 109.

Figure 10:
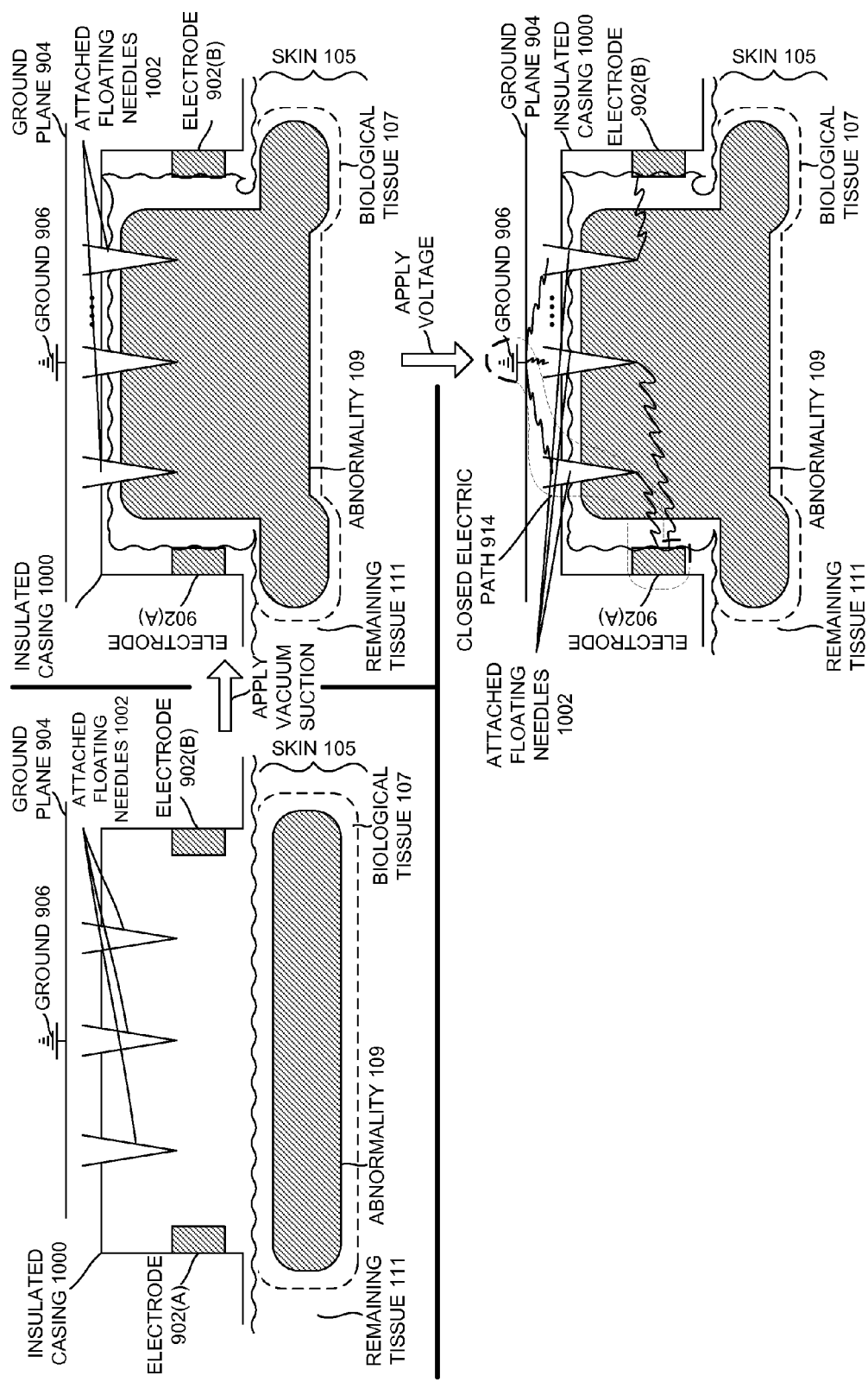
FIG. 10 illustrates another example scenario of eradication of an abnormality in a biological tissue by applying resonance frequency through a signal source using multiple attached needles attached to an insulated casing, in accordance with one or more embodiments.

FIG. 10 illustrates another example scenario of eradication of an abnormality 109 in a biological tissue 107 by applying resonance frequency through a signal source using multiple needles (e.g., attached floating needles 1002) attached to an insulated casing 1000, in accordance with one or more embodiments. The insulated casing 1000 may have the floating needles pre-coupled with the insulated casing 1000 before the application of vacuum suction as compared to insulated casing 900. In the insulated casing 900, the floating needles are not pre-coupled with the casing, rather the insulated casing 900 only has provisions for inserting the floating needles after vacuum suction. The provision may be holes on in the insulated casing through which the floating needles are inserted. The apparatus of FIG. 10 functions similar to the apparatus of FIG. 9. In one or more embodiments, the abnormality 109 in the biological tissue 107 may be sucked into the insulated casing 1000 by applying vacuum suction while inserting the attached floating needles 1002 into the abnormality 109. A voltage may be applied to a pair of electrodes 902 (A) and 902 (B) to maintain the electrodes 902 (A) and 902 (B) at a same potential compared to a ground 906 on a ground plane 904 which may be at an potential opposite to that of the electrodes. For example, the electrodes may be at a positive potential and the ground may be at a negative potential. The electric energy forms a closed electric path 914 between the electrode 902(A) and the ground plane 906 through the abnormality 109 and/or one among a plurality of floating needles. The closed electric path 914 may be formed when a potential difference is applied between the first pair of electrode 902(A) and the ground 904 and/or the second pair of electrode 902(B) and the ground 904. The potential difference may be set so as to match the characteristic resonance frequency of the abnormality 109.

Figure 11:
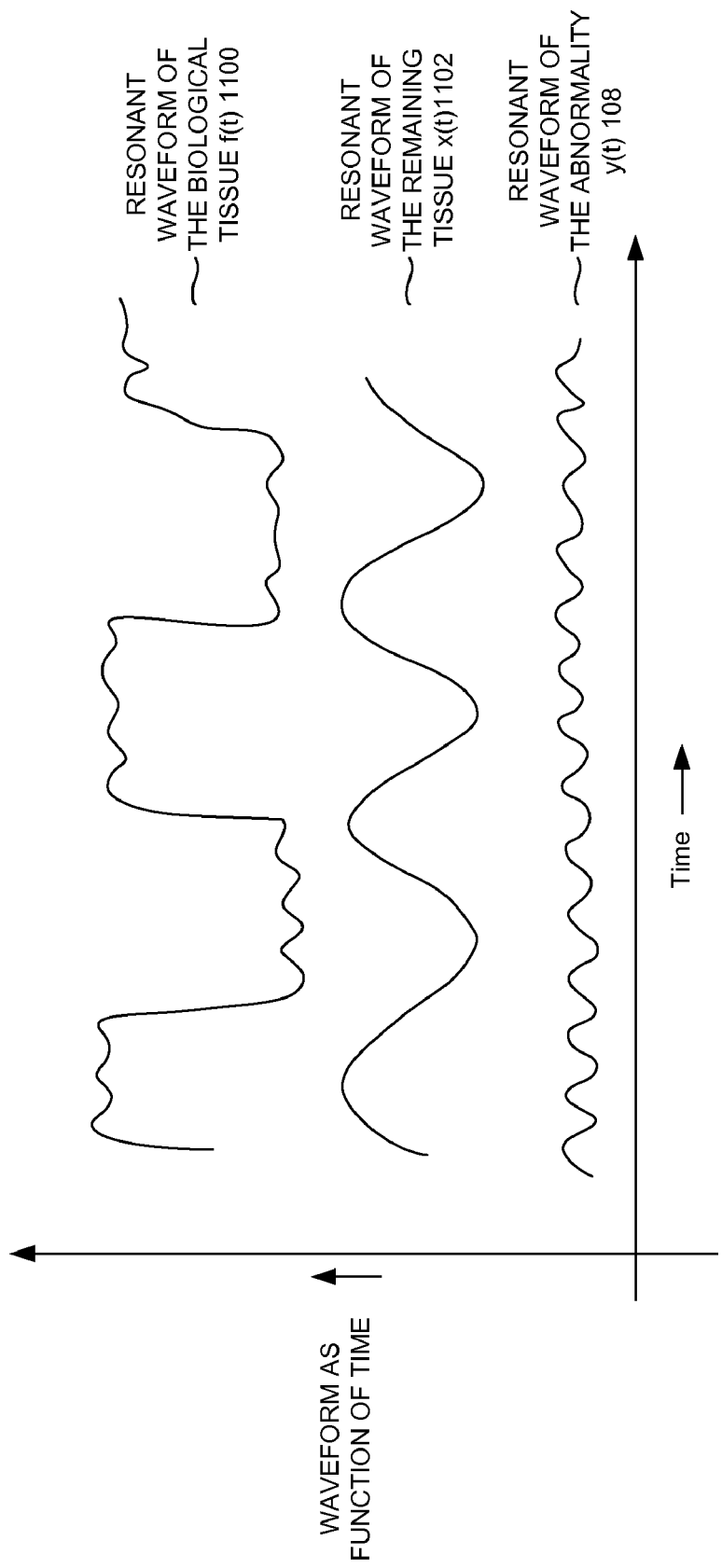
FIG. 11 shows a time domain representation of multiple resonant waveforms as a function of time, in accordance with one or more embodiments.
Figure 12A:
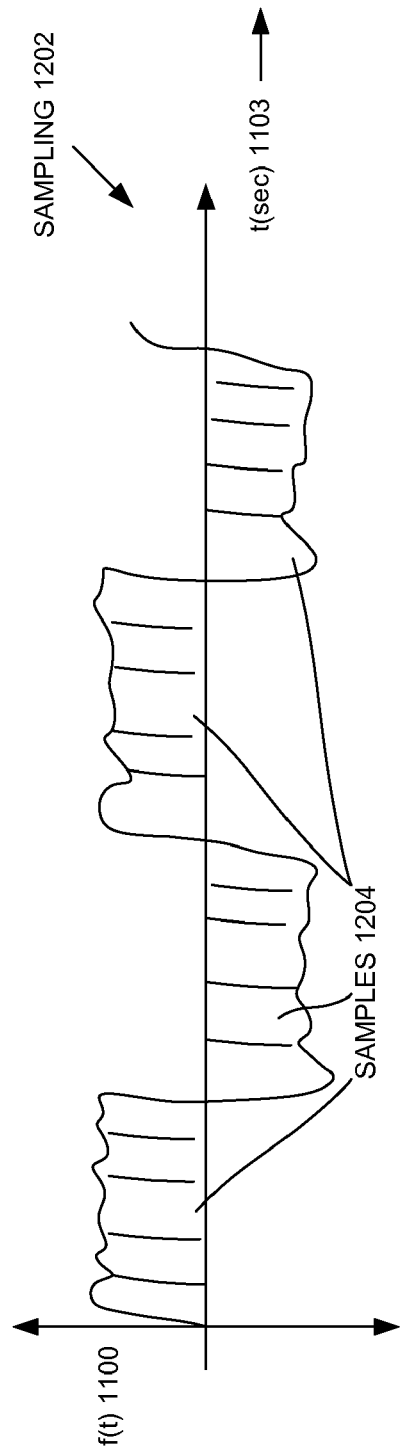
FIGS. 12A-12B illustrates segmentation of the combined resonant waveform of the biological tissue using a discrete Fourier transform, in accordance with one or more embodiments.
Figure 12B:
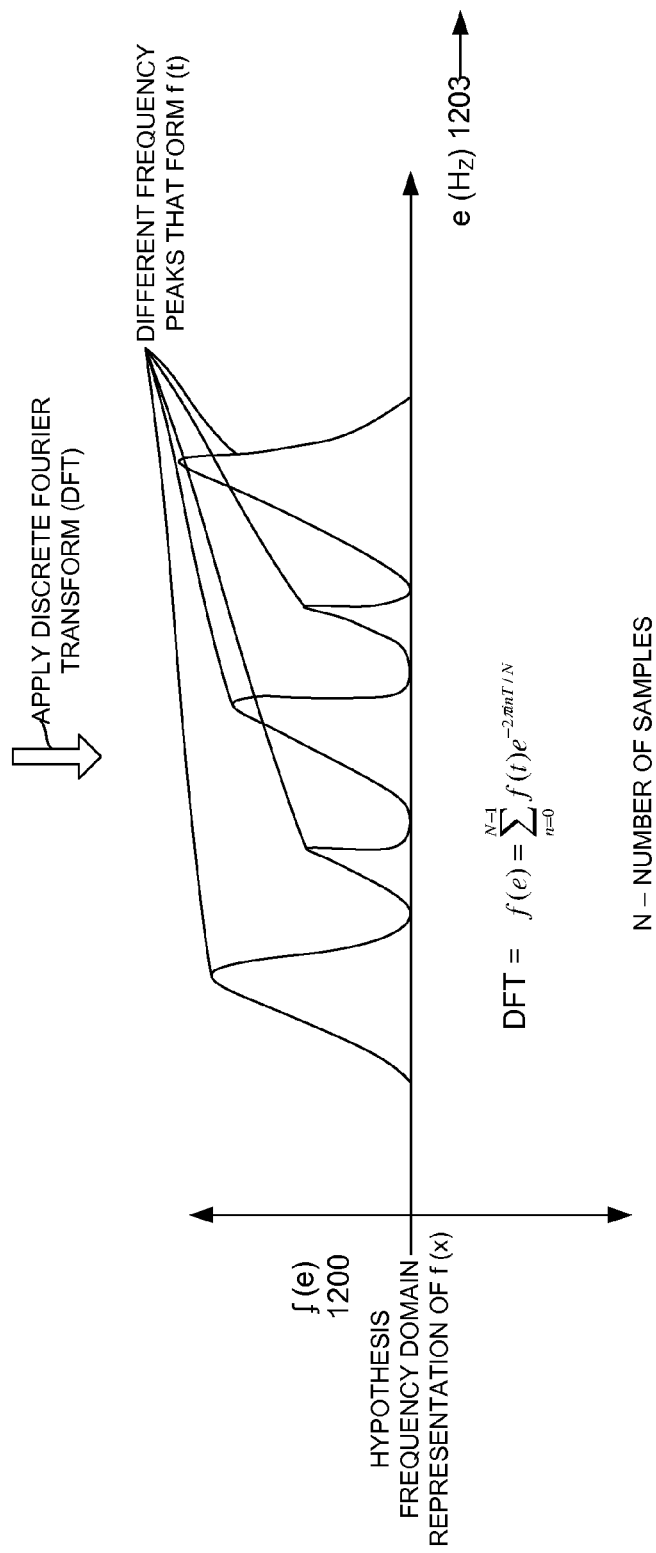

FIG. 11 is time domain representation of multiple resonant waveforms as a function of time. In one or more embodiments, a resonant waveform of the biological tissue 1100 (f(t)) may be a combination or a superimposition of a resonant waveform of the remaining tissue 1102 (x(t)) and a resonant waveform of the abnormality 108 (y(t)) as illustrated in FIG. 11. If the resonant waveform of the biological tissue 1100 (f(t)) may be a combination or a superimposition of a resonant waveform of the remaining tissue 1102 (x(t)) and a resonant waveform of the abnormality 108 (y(t)) as illustrated in FIG. 11, then the combined resonant waveform 1100 of the biological tissue 107 may be used to determine resonance frequency of the abnormality 109 in the biological tissue 107. In one or more embodiments, as illustrated in the detailed description of FIG. 2, the combined resonant frequency waveform 1100 of the biological tissue may be segmented into the resonant frequency waveform of the remaining tissue 1102 and the resonant waveform 108 of the abnormality 109. In one or more embodiments to segment the combined resonant frequency waveform 1100, a Fourier analysis function (e.g. a discrete Fourier transform) may be applied to the combined waveform 1100 of the biological tissue 107. Further, a split function may be applied to the combined waveform 1100 of the biological tissue 107 after applying the Fourier analysis function to separate the resonant waveform of the abnormality 109 from the combined waveform. The Fourier analysis technique used may be a discrete Fourier transform. FIGS. 12A-12B illustrates segmentation of the combined resonant waveform 1100 of the biological tissue using a discrete Fourier transform, in accordance with one or more embodiments. The discrete Fourier transform (DFT) given by equation (1) may be applied to the samples 1204.

$$DFT = f(e) = \sum_{n=0}^{N-1} f(t)e^{-2\pi i nT/N} \quad (1)$$

N may be number of samples 1204 obtained. FIG. 12A illustrates a time domain representation of the combined resonant waveform 1100 of the biological tissue 107, in accordance with one or more embodiments. The combined resonant waveform 1100 of the biological tissue 107 may be sampled at different intervals of time to obtain multiple samples 1204. On applying the DFT, the combined waveform 1100 in the time domain may be transformed to a frequency domain represented as f(e). f(e) may be the frequency domain representation of the combined resonant waveform 1100. The frequency domain representation of the combined waveform 1100 may include multiple peaks as illustrated in FIG. 12B. The peaks may indicate the dominant frequencies that form the combined waveform 1100. A split function may be applied to the frequency domain representation f(e) of the combined waveform 1100 to segment the dominant frequencies that form the combined waveform. The dominant frequencies may be the resonant frequency waveform 1102 of the remaining tissue 111 and the resonant frequency waveform 108 of the abnormality 109.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

What is claimed is:

1. A medical device, comprising:
a needle;
an electrode;
a processor programmed:
to automatically determine which portion of a biological tissue is associated with an abnormality in the biological tissue when a sample density of an immediate area surrounding the needle in the biological tissue matches a target density as determined based on the at least one of a chemical composition and a pigmentation of the abnormality, and
to calculate a resonance frequency to eradicate a presence of the abnormality based on at least one of the chemical composition and the pigmentation of the abnormality as determined through at least one of a conductivity, a capacitance, and an inductance of the abnormality; and
a signal source configured:
to electrically couple the needle with the electrode such that a closed circuit is formed when the needle and the electrode contact the biological tissue, and
to deliver the resonance frequency targeted to the abnormality through the biological tissue in a manner such that a delivery of the resonance frequency preserves a regeneration capability of a remaining tissue surrounding the biological tissue by monitoring a vibration of at least one of the remaining tissue and the biological tissue when the resonance frequency is applied to the biological tissue having the abnormality.

2. The medical device of claim 1:
wherein the processor is programmed to apply an algorithm to determine a length-of-time that the resonance frequency targeted to the abnormality is delivered,
wherein the algorithm is based on a regeneration pattern of a wound heal area encompassing the abnormality created when the abnormality was first introduced in the biological tissue,
wherein the algorithm is programmed to determine an age of when the abnormality was first introduced in the biological tissue, and
wherein the algorithm is programmed to determine a depth that the needle needs to enter the biological tissue to reach the immediate area having the target density.

3. The medical device of claim 1 further comprising:
a waveform segmentation module of the processor is programmed to segment a first resonant frequency waveform associated with the biological tissue from a second resonant frequency waveform associated with the abnormality, wherein the segmentation is performed based on a control sample of the remaining tissue and the biological tissue having the abnormality by applying a Fourier analysis function to a combined waveform of an afflicted area targeted for eradication of the abnormality and a split function to separate the waveforms; and
a resonant frequency calibration module of the processor is programmed to adjust the resonance frequency targeted to the abnormality through the biological tissue in a manner such that the delivery of the resonance frequency preserves the regeneration capability of the remaining tissue surrounding the biological tissue by monitoring the vibration of the at least one of the remaining tissue and the biological tissue when the resonance frequency is applied to the biological tissue having the abnormality.

4. The medical device of claim 1 wherein the abnormality is at least one of a foreign substance and an undesired manifestation.

5. The medical device of claim 4 wherein the foreign substance is a tattoo in a host living organism associated with the biological tissue.

6. The medical device of claim 4 wherein the undesired manifestation is at least one of a cancerous tumor, an acne, a lesion, a stretch mark, a skin condition, a scar, a burn, and an age spot.

* * * * *